United States Patent [19]

Brun et al.

[11] Patent Number: 4,849,696
[45] Date of Patent: Jul. 18, 1989

[54] APPARATUS FOR DETERMINIG THE STRENGTH AND DIRECTION OF A MAGNETIC FIELD, PARTICULARLY THE GEOMAGNETIC FIELD

[75] Inventors: Robert Brun, Balgach; Ernst Ramseier, Heerbrugg, both of Switzerland

[73] Assignee: Wild Heerburgg, AG, Heerbrugg, Switzerland

[21] Appl. No.: 190,583

[22] Filed: May 5, 1988

[30] Foreign Application Priority Data

May 11, 1987 [CH] Switzerland ............... 01777/87

[51] Int. Cl.4 ............................................. G01R 33/06
[52] U.S. Cl. ..................................... 324/252; 33/361; 324/247
[58] Field of Search ............... 324/252, 247, 253, 207, 324/208, 244; 338/32 R; 33/355, R, 363 Q, 361

[56] References Cited

U.S. PATENT DOCUMENTS

| | | | |
|---|---|---|---|
| 4,539,760 | 9/1985 | Marchant et al. | 33/361 X |
| 4,661,773 | 4/1987 | Kawakita et al. | 324/247 X |
| 4,683,535 | 7/1987 | de Ridder et al. | 324/252 X |
| 4,736,072 | 8/1988 | Katoh et al. | 324/253 |

Primary Examiner—Gerard R. Strecker
Assistant Examiner—Robert W. Mueller
Attorney, Agent, or Firm—Helfgott & Karas

[57] ABSTRACT

A toroidal or similar body (1) of a non-magnetic, insulating material, preferably glass fibre-reinforced plastic or ceramic is provided with at least three recesses for receiving in each case a corresponding one magnetoresistive sensor. The associated measuring directions of said sensors are orthogonal to one another. For producing a magnetic auxiliary field applied to the sensors, a coil is arranged on the body. for increasing the accuracy and reliability of the measured result, the body is provided with at least one further recess for receiving a further sensor. The measuring direction of the further sensor differs from that of other sensors and forms preferably the same angle with the other measuring directions. The body can be in multipart form and is in particular made from two identical parts.

The apparatus can be used in electronic compasses and for north finding devices.

16 Claims, 2 Drawing Sheets

APPARATUS FOR DETERMINIG THE STRENGTH AND DIRECTION OF A MAGNETIC FIELD, PARTICULARLY THE GEOMAGNETIC FIELD

BACKGROUND OF THE INVENTION

The invention relates to an apparatus for determining the strength and direction of a magnetic field comprising a plurality of magnetoresistive sensors, each of which is associated a different measuring direction, and a coil for producing a magnetic auxiliary field applied to the sensors.

Such an apparatus is described on pages 8 to 10 of the brochure "Anwendungen der Magnetfendsensoren KMZ 10", Technische Information philips-VALVO 861105, 1986. According to the brochure, with two sensors arranged at right angles to one another in a coil, a compass can be produced and both sensors can be switched over with one coil.

If a magnetoresistive sensor is used for determining the strength and direction of a magnetic field, it is necessary to define a privileged, preferred or measuring direction on the sensor by means of a magnetic auxiliary field acting thereon. The auxiliary field serves to prevent the random tilting of the magnetic domains under the influence of varying magnetic fields, or it at least brings about the restoration of a clearly defined magnetization state of the sensor following the fading away of a strong magnetic disturbance acting thereon. The sensor measures the component of a magnetic field which is parallel to the measuring direction or the auxiliary field.

It is known from the aforementioned brochure to produce a magnetic auxiliary field by a current-carrying coil. It is also known to use a coil through which a timed current flows if a weak field, such as e.g. the geomagnetic field is to be determined, the auxiliary field being switched out at the time of determination, in order to avoid the sensitivity of the sensor being reduced through the auxiliary field. It is also known, through the systematic reversal of the magnetism of the sensor, to avoid the effect of the strong temperature-dependent DC offset which, as a result of manufacture, varies from one individual sensor to the other.

However, a complete determination of the strength and direction of the geomagnetic field in a precise electronic compass requires three sensors with measuring directions not coplanar to one another (in addition tilt or gravity sensors are required for determining the horizontal plane). In connection with this problem, the aforementioned brochure makes the following statement: "For measurements in the third direction (at right angles to the XY-plane) a second coil must be used. It has in fact been found that arrangements with only one coil for three directions (and therefore for three sensors) do not provide satisfactory solutions."

When using several straight coils (solenoids), as proposed in the aforementioned brochure, there are certain disadvantageous restrictions concerning the reciprocal arrangement of the coils. For example, it is necessary to provide a larger spacing between the coils or to shield the alternating field of each coil to prevent reciprocal influencing.

Another disadvantage of the use of open coils is that each freely irradiates at its ends the auxiliary field, which leads to problems of electromagnetic compatibility and to losses particularly in the case of high frequency shielding, i.e. to an increased power requirement for the apparatus supply.

However, it is desirable to simultaneously measure the three components of the magnetic field in the three-dimensional space in order to exclude measuring errors occurring in the case of a rapidly moving measurement point,(e.g. on a vehicle) or a rapidly varying magnetic field, if the measurement of the different components takes place successively or the measurement of one of the components with respect to the two others takes place with a marked time lag.

SUMMARY OF THE INVENTION

It is an object of the present invention to provide apparatus wherein three sensors can be subjected simultaneously to the action of the same clearly defined auxiliary field for the simultaneous determination of the three components of the magnetic field in three-dimensional space, without having to accept the aforementioned disadvantages of using more than one coil.

According to the invention this apparatus has the combination of features given in claim 1. Advantageous further developments of the inventive apparatus and a use thereof can be gathered from the corresponding dependent claims.

The inventive apparatus makes it possible to measure the three components of the magnetic field in the three-dimensional space not only at the same time, but substantially at the same location, because the apparatus dimensions can be kept much smaller than if the known apparatus with three sensors is used. In addition, there is no need to operate the apparatus in a predetermined spatial position (i.e. levelled beforehand). These possibilities offer important advantages when using the apparatus as an electronic compass in rapidly moving air, sea or land vehicles.

When the coil producing the auxiliary field has the inventive form disclosed herein, the auxiliary field within the coil is substantially homogeneous or uniform and namely also in the small recesses for receiving the sensors and their connections. This field is sufficiently uniform for using the apparatus as an electronic compass. In addition, the auxiliary field strength can be easily calculated within a toroidal coil. In order to improve the uniformity of the auxiliary field and make available more space for receiving the sensors, whilst ensuring that all the sensors are subject to the action of the auxiliary field with the same intensity, the body can have a shape derived from a torus, in that the imaginary centre line of the torus, always remaining in the same plane, is shaped to a closed line with portions of different curvature. For example, in the vicinity of the sensors, the centre line can have straight portions and arcuate portions, which are alternately subsequently interconnected.

Particularly for using the apparatus as an electronic compass in rapidly moving air, sea or land vehicles, it is particularly advantageous that the apparatus can have a compact construction and that the reciprocal position of the sensors is immovable.

As in the case of the known, aforementioned apparatus, it is possible in the case of the inventive apparatus to avoid the effect of the temperature-dependent DC offset resulting from manufacture through the systematic magnetism reversal of the sensors.

Finally, the inventive apparatus avoids the aforementioned disadvantages linked with the presence of coil ends, namely problems with electromagnetic compatibility and power losses.

Reference is also made to the following literature relating to magnetoresistive sensors manufactured from permalloy and in thin film technology, as well as the use thereof in data technology, measurement technology and navigation: "Magnetoresistive Sensoren", Technische Information Philips -VALVO 840323, 1984, 8 pages; "The permalloy magnetoresistive sensor—properties and applications", W. Kwiatowski and S. Tumanski, J. Phys. E. Sci. Instrum., 19, 1986, pp 502–515; "Magnetoresistive permalloy sensors and magnetometers", W. Kwiatowski and S. Tumanski, Archiwum Elektrotechniki, 32, 1983, pp 55–64.

In connection with the technological background concerning the principle and use of magnetoresistive sensors reference is made to the following literature: "The magnetoresistive sensor—a sensitive device for detecting magnetic field variation", U. Dibbern and A. Petersen, Electronic Components and Applications, 5/3, 1983, pp 148–153; "Drehwinkelmessung mit Magnetfeldsensoren", G. Reiniger, Elektronik, 23, 1986, pp 129–136; "Magnetoresistive response of small permalloy features", S. K. Decker and C. Tsang, IEEE Trans. on Magnetics, Mag16/5, 1980, pp 643–645; "Magneto-resistance in laminated Nife films", J.A.C. van Oyen et al., J. Appl. Phys., 53/3, 1982, pp 2596–2598.

DETAILED DESCRIPTION OF PREFERRED EMBODIMENTS

Figure 1:
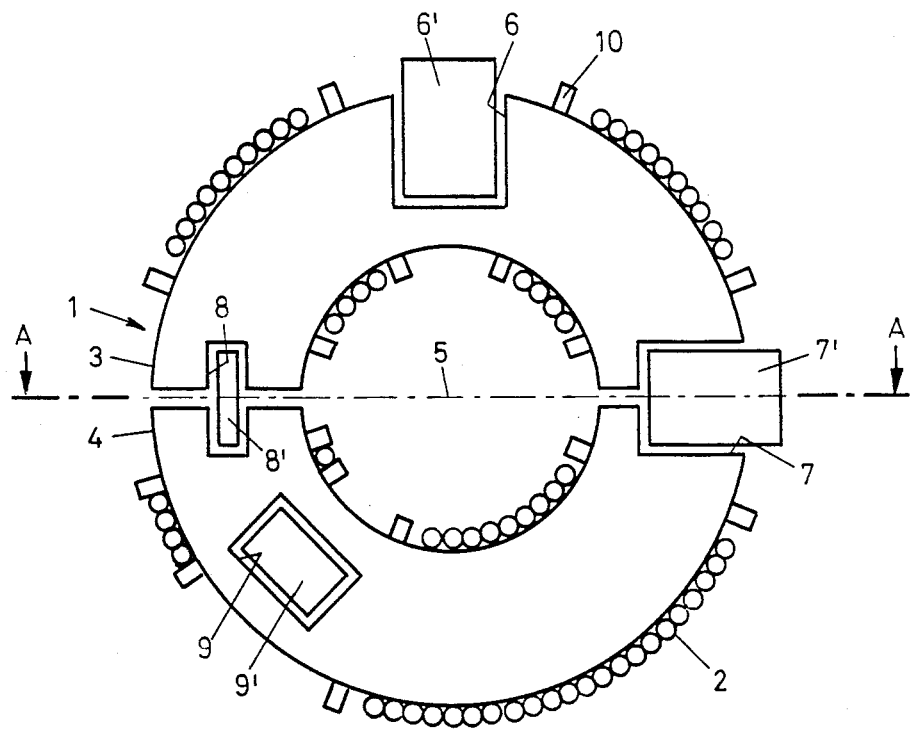
FIG. 1 is a diagrammatic view of a first embodiment of a construction of the inventive apparatus shown in section through its central plane.
Figure 2:
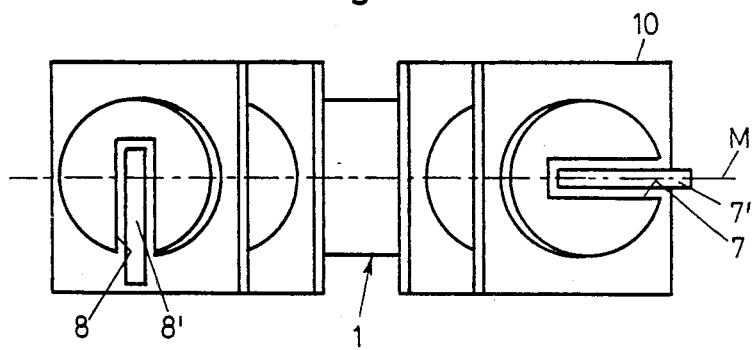
FIG. 2 is a diagrammatic view of the construction of FIG. 1 in section through the plane designated A—A in FIG. 1.

FIGS. 1 and 2, which illustrate the invention in a diagrammatic representation, show a first embodiment of the inventive apparatus with a susbstantially toroidal body 1. The material of said body can be a random non-magnetic insulating material, e.g. a plastic or ceramic. When plastic is used, the material of body 1 is preferably constituted by a known glass fibre-reinforced plastic, such as a glass fibre-reinforced epoxy resin.

FIG. 1 shows body 1 in section through its central or medium plane M (the plane of the circular centre line of the torus) and in FIG. 2 in the diametral section through the plane designated by line A—A in FIG. 1. Body 1 forms the core of a toroidal coil 2, which is substantially, i.e. with the hereinafter explained exceptions, wound in regular turns onto body 1. FIG. 1 only diagrammatically shows a few turns of coil 2 in cross-section (more particularly oversized), whilst FIG. 2 does not show the turns which should be visible therein, because a turn in the correct scale of FIG. 2 would be scarcely recognizable and an oversized representation of a single turn or a correct representation of the complete coil would impede the understanding of FIG. 2.

In order to facilitate the manufacture of the winding and the assembly of the apparatus, body 1 is formed from two parts 3 and 4. Preferably these two parts 3 and 4 are of the same size, so that they are joined along a diametral plane 5 of body 1. However, if necessary, toroidal body 1 can also be made from more than two parts. The fixing of the two parts 3 and 4 to one another is not shown and can e.g. take place by bonding and/or fixing to a common substantially. FIG. 1 shows the two parts 3 and 4 with a small intermediate spacing, but this is only provided as a drawing measure for clarifying the representation and in reality the two parts 3 and 4 engage with one another.

Body 1 is provided with three recesses, serving to receive in each case one magnetoresistive sensor 6', 7', 8', Such magnetoresistive sensors are essentially rectangular small plates, which in each case have one measuring direction, in which as a result of the magnetoresistive characteristics thereof they are sensitive to the field strength of a magnetic field applied thereto. The component of this field strength in the measuring direction of the sensor is converted by the latter into an electric signal. FIGS. 1 and 2 show the sensors 6', 7', 8', with a marked spacing from the wall of the associated recess 6, 7, 8, but this is only a drawing measure for clarifying the representation. In reality, the sensors are snugly located in the recesses, so that their position is precisely defined and they are immovably fixed therein in a random manner, e.g. by bonding. The adhesive is also used for cooling the sensors, in that it dissipates the heat produced electrically therein into body 1.

In the vicinity of sensors 6', 7', 8' the winding of coil 2 cannot pass quite as regularly as in the area between the sensors, i.e. the particular region of a recess and the associated sensor is skipped in an appropriate manner, e.g. by subdividing the winding or changing the winding pitch. These exceptions concerning the regularity of the winding are not important, so that the complete apparatus with the recesses and the sensors located therein is substantially toroidal.

Subdividing body 1 into two makes it much easier to apply the windings of coil 2. Aids such as webs, disks or plates 10, e.g. made from plastic, can be arranged thereon or can be manufactured as an integral part of the coil body and can be used for fixing the complete toroidal structure to a substantially.

In body 1 the recesses are oriented in such a way that the measuring directions 6', 7' and 8' of the three sensors are orthogonal to one another. Thus, three components of the field strength to be measured orthogonal to one another are determined, which makes it possible to determine the strength and direction of the magnetic field to be measured.

In order to increase the accuracy and reliability of the measurement result, body 1 can be provided with at least one further sensor 9', besides sensors 6', 7', 8', in each case, in a corresponding recess. The angular position of the additional sensors is chosen in accordance with the particular objective. In the embodiment shown in FIGS. 1 and 2, body 1 is provided with a fourth recess 9, which serves to receive a fourth magnetoresistive sensor 9'. The measuring direction of sensor 9' fundamentally differs from the measuring directions of sensors 6', 7', 8'. In order that sensor 9, can fulfill its function in the same way in conjunction with each of the three other sensors 6', 7', 8', it is preferably arranged in such a way that its measuring direction is at the same angle to each of the three other measuring directions of sensors 6', 7', 8', which are orthogonal to one another. In other words, if it is imagined that the measuring directions of sensors 6, 7' and 8, form the edges of a cube, then the measuring direction of sensor 9, is located on one of the space diagonals of said cube. The measured value determined in this case with sensor 9, and in the general case with the other sensors is intended to be combined with the measured values determined by the three other sensors 6', 7' and 8' so that, as mentioned e.g. hereinbefore, the accuracy and reliability of the measured result can be increased.

Coil 2 is used for producing a magnetic field applied to sensors 6', 7', 8' and 9'. The purpose of this auxiliary field is known per se and has been explained hereinbefore.

Figure 3:
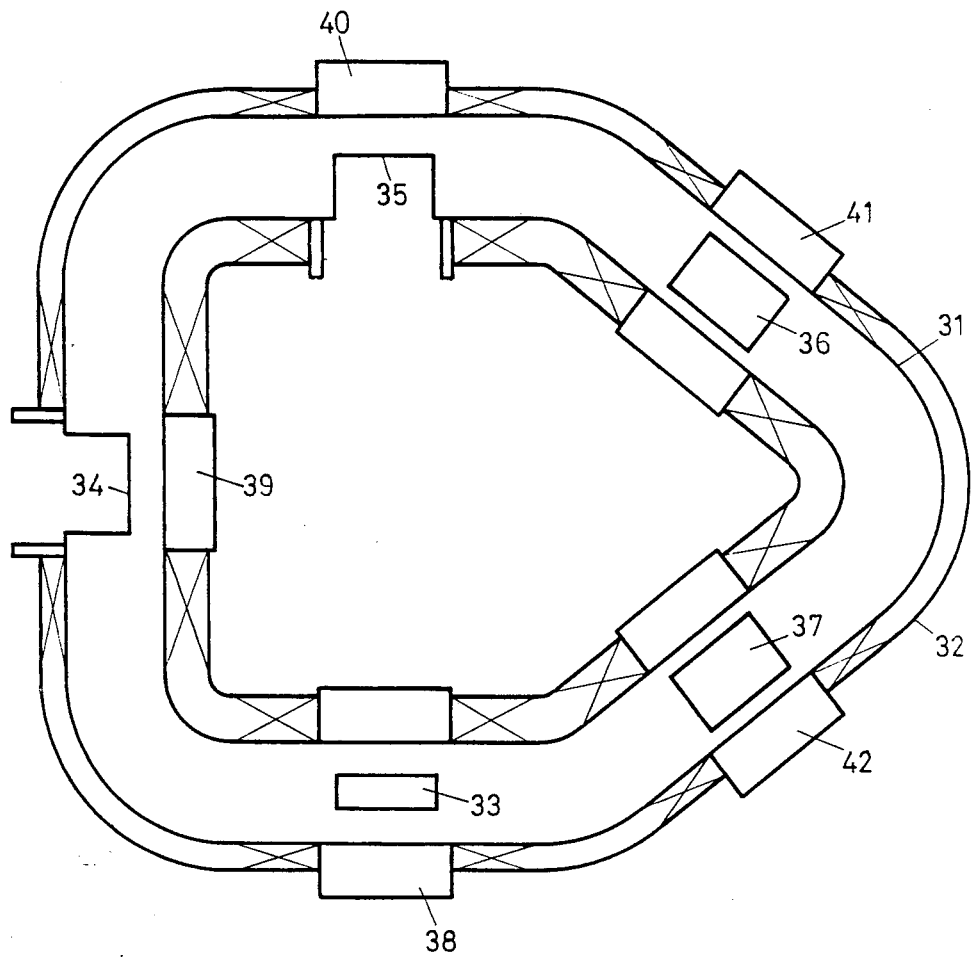
FIG. 3 is a diagrammatic view of a second embodiment of the construction of the inventive apparatus shown in section through the median plane thereof.

FIG. 3, which also illustrates the invention in a diagrammatic representation, shows a second embodiment of the inventive apparatus with a body 31 having a different shape from that in FIG. 1. In this embodiment, the shape of body 3 is derived from that of a torus by deforming the imaginary centre line of said torus, said imaginary centre line always remaining in the same plane, still forming a closed line and now has portions of different curvature (in the case of a zero curvature the portions are linear). Thus, body 31 has a shape topologically equivalent to a torus and which can be referred to as a deformed ring. Further details will be given hereinafter. The material of body 31 has been described in conjunction with body 1. Body 31 can be formed from two or more parts, as described in connection with FIG. 1.

FIG. 3 shows body 31, identically to the representation mode of FIG. 11, in section through its central plane. Body 31 forms the core of a coil 32, which substantially, i.e. with the exceptions illustrated in conjunction with FIG. 1, is wound in regular turns onto body 31. FIG. 3 diagrammatically shows said coil 32 in section. Body 1 is provided with five recesses, 33, 34, 35, 36 and 37, which serve to receive in each case one, not shown, magnetoresistive sensor of the type described in conjunction with FIG. 1. In the vicinity of recesses 33, 34, 35, 36 and 37, the imaginary centre line of body 31 is linear, i.e. each recess is located in one of five substantially cylindrical portions of body 31. The imaginary centre line of body 31 is curved between these cylindrical portions. Thus, along the imaginary centre line there are alternately five linear and five substantially arcuate portions tangentially connected thereto so as to constitute a closed, unbroken curve. The body formed round this imaginary centre line has a substantially circular cross-section and therefore expressed pictorially is a deformed torus.

In order to increase the strength of body 1 or 31 in the vicinity of recesses 6, 7, 8, 9 or 33, 34, 35, 36 and 37 and in order to obtain bearing surfaces firmly connected to the median plane, it is possible to fit parallelepipedic reinforcements 38, 39, 40, 41 and 42 in place of plates 10.

Like coil 2 in FIG. 1, coil 32 is interrupted in the vicinity of recesses 33, 34, 35, 36 and 37, i.e. the particular region of a recess and the associated sensor is skipped in an appropriate manner, e.g. by subdividing the winding or modifying the winding pitch. Once again, these exceptions to the regularity of the winding are not important.

Within body 31, recesses 33, 34, 35, 36 and 37 are differently oriented, in order to give the five sensors different measuring directions and consequently increase the accuracy and reliability of the measured result, as described in connection with FIG. 1.

In the construction according to FIG. 3, e.g. it is possible to arrange in the three recesses 33, 34, 35 sensors with measuring directions orthogonal to one another like sensors 6', 7', 8' in FIG. 1, whilst in the two recesses 36, 37 are arranged additional sensors like sensor 9, in FIG. 1. These five sensors are jointly biased by the magnetic field of the common coil 32.

The described apparatus of which various embodiments are shown in FIGS. 1 to 3 is particularly suitable for determining the strength and direction of the geomagnetic field, e.g. for use in a device for finding the magnetic north in an air, sea or land craft. As all three components of the geomagnetic field are determined, the body 1 can be installed in random position in the vehicle or in the vehicle compass. However, the accuracy of finding north is increased if a position is chosen, in which none of the three components continuously dominates. In the preferred position, body 1 is so incorporated into the device for finding the magnetic north, that the median plane M of body 1 forms an angle with the horizontal plane. This angle is so determined that in the case of the device pointing north, at least two sensors provide equally large signals and in middle geographical latitudes is approximately 20°.

The apparatus shown in FIGS. 1 to 3 is obviously also suitable for determining the strength and direction of magnetic fields other than the geomagnetic field, if the field strength thereof is of the same order of magnitude as the geomagnetic field, or differs therefrom only by up to two orders of magnitude, i.e. between $10^{-2}$ and $10^2$ times those of the geomagnetic field.

In a specific embodiment of such an apparatus use is made of magnetoresistive sensors of a commercially available type having a rectangular sensitive surface of approximately 1.6 mm side length. The sensors are embedded in plastic and appear as rectangular plates with a side length of approximately 5 mm and a height of approximately 1.8 mm (further details are given in the first-mentioned publication). On these sensors the magnetic auxiliary field must be approximately 3 kA/m. As a condition for the uniformity of the auxiliary field over the entire magnetically sensitive range of each sensor, it can be established that the transverse components of the auxiliary field resulting from the curvature of its field lines in the toroidal or a torus-identical body, at no point of the sensitive range may be larger than a predetermined fraction of the longitudinal component of the auxiliary field on the centre line of the body. It is possible to calculate from the dimensions of the magnetically sensitive range of the sensors, as well as the maximum permitted ratio of the transverse to the longitudinal component, e.g. 10%, the smallest permissible radius at the particular point of the body using simple geometrical and trigonometrical considerations.

What is claimed is:

1. An apparatus for determining the strength and direction of a magnetic field comprising:
  a nonmagnetic insulating body having a shape topologically equivalent to a torus, said body having at least three spaced apart recesses;
  at least three magnetoresistive sensors, each sensor being disposed in a corresponding one of said recesses; and
  a coil wound about said body and having substantially regular turns, said coil for generating a homogeneous auxiliary magnetic field through said body and shielding said sensors from external magnetic perturbations.

2. The apparatus as set forth in claim 1 wherein each sensor has a different measuring direction associated therewith.

3. The apparatus as set forth in claim 2 wherein there are three sensors, and the measuring directions are mutually orthogonal.

4. The apparatus as set forth in claim 2 wherein the body has four recesses and there are four sensors, three of said sensors having associated therewith mutually orthogonal directions, the fourth sensor having an associated direction differing from each of the mutually orthogonal directions.

5. The apparatus as set forth in claim 4 wherein each of the three mutually orthogonal directions are orthogonal to one another as the space diagonals of a cube to the edges thereof and the measuring direction associated with the fourth sensor is disposed at the same angle with respect to each of the other measuring directions.

6. The apparatus as set forth in claim 5 wherein the body is constructed in two mating parts.

7. The apparatus as set forth in claim 6 wherein the two parts when interconnected are interconnected along a diametrical plane of symmetry.

8. A method for using the apparatus as defined in claim 2 comprising the steps of disposing the apparatus in a magnetic field having a field strength falling within the range defined by the geomagnetic field multiplied by a factor having a lower limit of $(10^{-2})$ and an upper limit of $(10^2)$; and using the apparatus to measure said field strength.

9. The method as set forth in claim 8 for using the apparatus to find magnetic north wherein the body has a median plane disposed at an angle with respect to the horizontal plane which is dependent upon the geographical latitude of the location at which the measurement is made.

10. The method of claim 9 wherein said angle in middle latitudes is approximately 20°.

11. The apparatus as set forth in claim 1 wherein said body is a glass fiber-reinforced plastic.

12. The apparatus as set forth in claim 1 wherein said body is a ceramic.

13. The apparatus as set forth in claim 1 wherein the body has a substantially toroidal shape.

14. The apparatus as set forth in claim 13 wherein the body is constructed in multipart form.

15. The apparatus as set forth in claim 1 wherein the shape of the body is derived from a torus and the center line of the body as compared to the center line of a torus lies in the same plane but defines a closed line with portions of different curvature.

16. The apparatus as set forth in claim 15 wherein the body is constructed in multipart form.

* * * * *